United States Patent [19]

Williams

[11] 4,063,100
[45] Dec. 13, 1977

[54] RADIOGRAPHIC TABLE WITH MOVABLE GRID ASSEMBLY

[76] Inventor: Lee B. Williams, 396 Dayloma Ave., Ventura, Calif. 93003

[21] Appl. No.: 729,420

[22] Filed: Oct. 4, 1976

[51] Int. Cl.² .............................................. A61B 6/06
[52] U.S. Cl. ................................................. 250/452
[58] Field of Search ...................................... 250/452

[56] References Cited

U.S. PATENT DOCUMENTS 2,767,323   10/1956   Stava et al. ........................... 250/452

FOREIGN PATENT DOCUMENTS 1,155,875   12/1957   France ................................. 250/452

Primary Examiner—Alfred E. Smith
Assistant Examiner—T. N. Grigsby
Attorney, Agent, or Firm—Ralph B. Pastoriza

[57] ABSTRACT

A radiographic table is provided with the usual carriage for supporting a film cassette and a grid assembly. The grid assembly itself is resiliently mounted in the carriage for oscillating movement in a transverse direction during exposure of a patient's body to radiation to avoid the presence of grid lines on the developed film. The oscillatory motion is effected by a magnetic coupling so that no physical contacting of the grid assembly is necessary to effect the desired movement.

4 Claims, 4 Drawing Figures

U.S. Patent  Dec. 13, 1977  4,063,100
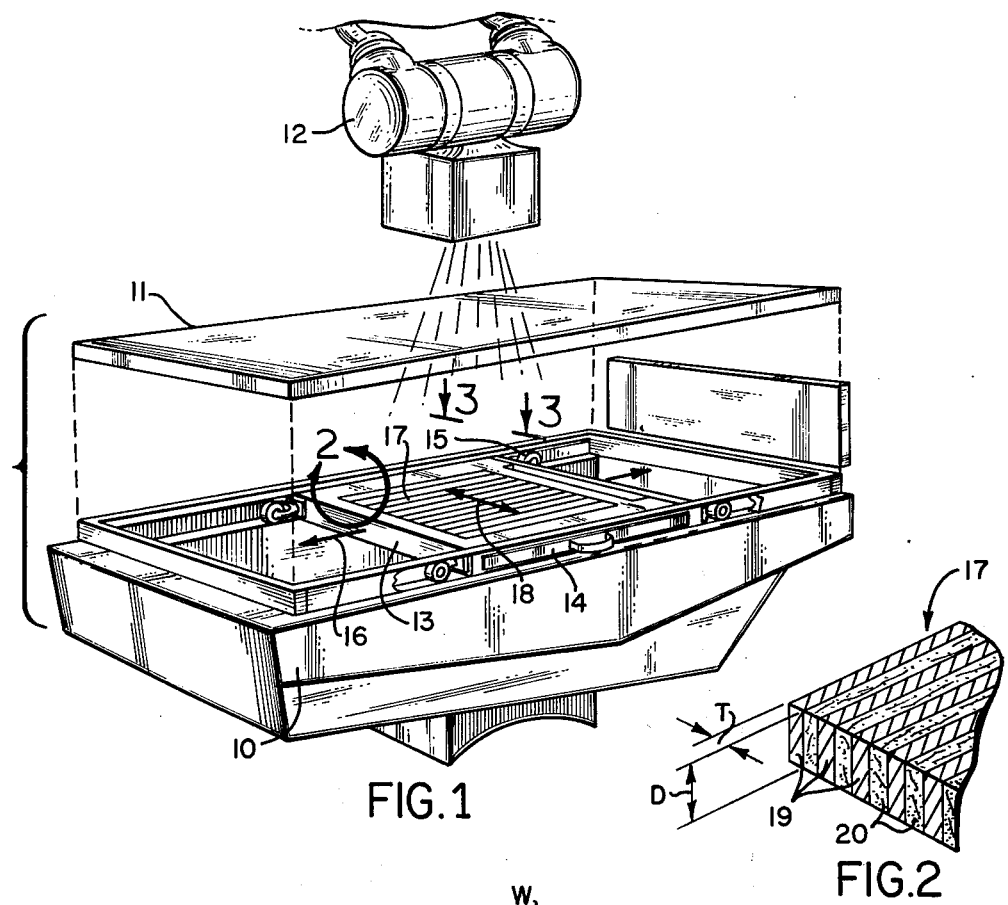
FIG.1
FIG.2
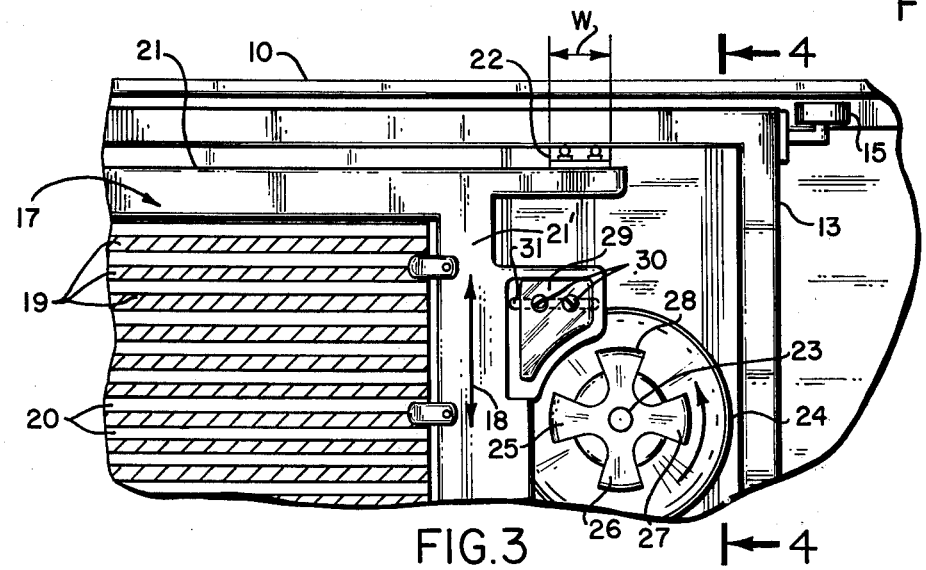
FIG.3
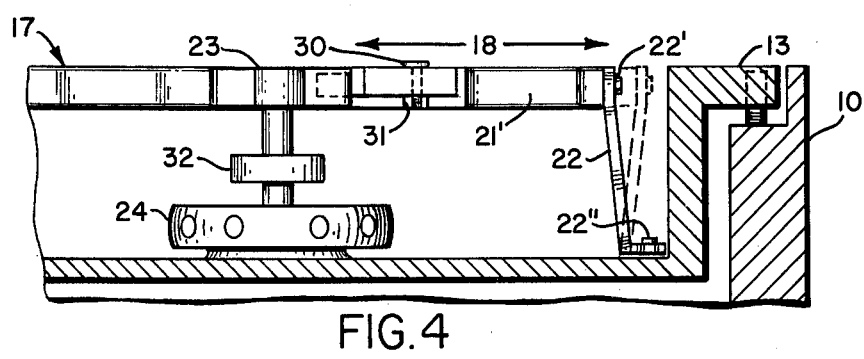
FIG.4

RADIOGRAPHIC TABLE WITH MOVABLE GRID ASSEMBLY

This invention relates generally to radiographic tables and more particularly to an improved means for moving the grid assembly associated with such table.

BACKGROUND OF THE INVENTION

It is well established practice to employ a grid when making radiographs (X-ray pictures) of various portions of a patient's body when the part to be examined is greater than 10cm. In the case of a radiographic table, there is normally provided a carriage which supports a film cassette arranged to move beneath a cover transparent to the X-rays. The film can thus be positioned under different portions of the patient's body while lying on the cover. The grid itself is also carried on the carriage immediately above the film and beneath the patient.

The function of the grid is to absorb scattered radiation passing through the patient's body to the film. The grid itself in this respect includes multiple parallel strips of lead or X-ray absorbing material held in specific spaced relationship by wood or plastic strips.

With the foregoing arrangement, it is found that superior radiographs can be obtained. On the other hand, faint parallel lines will show up on the developed picture resulting from the presence of the grid. To overcome this latter difficulty, it is common practice to move the grid in a direction transverse to the direction of the strips during exposure, this motion being just sufficient to avoid "photographing" the grid itself along with the desired image.

While vast improvements have been made in radiographic tables and grid structures, there has been little if any advance in the means provides for moving the grid during exposure. Generally, such systems as are used are mechanical in nature will simply oscillate the grid back and forth. There are two major problems with such arrangements. First, the mechanical vibrating or moving of the grid is noisy to the extent that it can alarm the patient possibly resulting in the patient himself moving during exposure, thus resulting in a blurred image. Second, the mechanics involved to move the grid can result in vibrations of the table itself, or carriage supporting the grid and film also resulting in blurring. This latter problem has become more pronounced when shorter exposures require faster grid movement.

BRIEF DESCRIPTION OF THE PRESENT INVENTION

With the foregoing considerations in mind, the present invention is directed to an improved radiographic table with a movable grid assembly wherein the means for moving or oscillating the grid during exposure are such as to avoid any type of noise which might alarm a patient and moreover, minimize deleterious movements resulting from the oscillation of the grid.

Towards the foregoing ends, the present invention contemplates the provision of a table bed frame for the radiographic table with a carriage for supporting a film cassette longitudinally movable to selected positions between the head and foot of the bed frame. A grid assembly in turn is provided together with resilient means preferably in the form of flexure type leaf springs mounting the grid assembly to the carriage for transverse oscillating movement. The carriage further includes movable magnetic responsive means carried on the carriage and a permanent magnet in turn is secured to the grid assembly in magnetic field coupling relationship to the movable magnetic responsive means. The arrangement is such that movement of the responsive means past the magnet in a direction having a transverse component results in transverse oscillatory movement of the grid assembly relative to the carriage.

Since the foregoing means does not involve any physical contact between the magnetic responsive means effecting movement of the grid and the grid assembly itself, it is extremely quiet. Further, the resilient mounting arrangement functioning similarly to flexures assures a very quiet oscillatory movement with minimum vibrations resulting therefrom in the carriage and table structure itself.

BRIEF DESCRIPTION OF THE DRAWINGS

A better understanding of this invention will be had by referring to a preferred embodiment thereof as illustrated in the accompanying drawings in which:

FIG. 1 is an exploded perspective view of the radiographic table with a movable grid assembly in accord with the present invention;

FIG. 2 is a greatly enlarged fragmentary perspective view of a portion of the grid assembly within the circular arrow 2 of FIG. 1;

FIG. 3 is a fragmentary plan view of the table of FIG. 1 looking in the direction of the arrows 3—3; and, FIG. 4 is a fragmentary end view partly in cross section looking in the direction of the arrows 4—4 of FIG. 3.

DETAILED DESCRIPTION OF THE PREFERRED EMBODIMENT

Referring to FIG. 1 there is shown a radiographic table made up of a table bed frame 10 and a removable cover or bed surface 11 shown exploded above the frame to expose the interior portions thereof. Conventional radiation equipment such as an X-ray machine is shown at 12 above the table bed.

A carriage 13 arranged to receive a film cassette as by a tray type drawer 14 is mounted on the bed frame as by appropriate rollers one of which is shown at 15 for longitudinal movement to selected positions between the head and foot of the bed frame as indicated by the arrow 16.

In addition to the film cassette tray, the carriage 13 also supports a grid assembly designated generally by the numeral 17. As will become clearer as the description proceeds, the grid assembly 17 is resiliently mounted to the carriage 13 for transverse oscillating movement as indicated by the double-headed arrow 18.

Referring to FIG. 2, details of the grid portion of the grid assembly 17 are shown. Thus, the grid includes a series of parallel strips of lead 19 of a given thickness T such as 1/64th of an inch held in side-by-side spaced relationship by a similar series of strips of wood or plastic material 20. The thickness of the plastic material may correspond to that of the lead strips, the lead strips and this plastic material having a depth D of about ⅛ of an inch.

As described briefly heretofore, the purpose for the grid is to avoid secondary scattering of the radiation from the machine 12 of FIG. 1 when making a radiograph of a portion of a patient lying on the cover 11 beneath the machine. As also mentioned, it is desired to impart a movement to the grid assembly during exposure so that grid lines will not show up on the developed picture.

The manner in which the desired oscillatory type transverse movement of the grid depicted by the double-headed arrow 18 of FIG. 1 is effected in accord with the present invention will now be understood by referring to FIGS. 3 and 4.

Referring to the left portion of FIG. 3, the grid made up of the lead strips 19 and separating strips 20 is held in a grid holder 21 completing the grid assembly 17. This grid holder in turn is resiliently mounted to the carriage 13 by a flat leaf type spring 22. The flat leaf type spring 22 has a sufficient width W in a longitudinal direction; that is the direction of the grid strip, that the grid assembly is constrained from movement in a longitudinal direction but is free to resiliently move back and forth in a transverse direction again indicated by the double-headed arrow 18 reproduced in FIG. 3. Essentially, the flat leaf type spring functions as a flexure and there are provided further leaf springs on the opposite side of the holder 21, there preferably being a total of four such resilient supports.

Within a portion of the carriage 13 there is disposed a movable magnetic responsive means in the form of a rotor 23 arranged to be rotated by a motor 24 in a plane including the plane of the grid assembly 17 adjacent to a side 21' of the grid assembly. In the particular embodiment disclosed, the rotor 23 includes four radially directed poles of magnetic responsive material indicated at 25, 26, 27, and 28.

Secured to the adjacent side 21 of the film grid assembly 17, there is provided, in turn, a permanent magnet 29. This magnet is preferably secured as by non-magnetic screws 30 passing through a slot 31 formed in the adjacent side 21' of the grid assembly. The magnet supporting portions are insulated and of non-magnetic material. The arrangement is such that the magnet 29 can be moved in a longitudinal direction to vary the spacing between the magnet and any one of the poles of the rotor 23.

The foregoing arrangement can better be understood by referring to the fragmentary end view of FIG. 4 wherein it will be noted that the plane of rotation of the rotor 23 coincides substantially with the plane of the grid assembly 17, the permanent magnet 29 also being positioned in this plane. In the particular embodiment disclosed, the motor 24 for driving the rotor 23 does so through the intermediary of a gear box 32 so that the rotational rate of the rotor 23 can be appropriately adjusted.

The leaf type spring resilient mount for the grid assembly 17 to the carriage 13 will also be clear from FIG. 4 wherein it will be noted that opposite ends of the flat leaf type spring 22 are secured to the grid assembly 17 as at 22' and the carriage as at 22". The small oscillatory movement of the grid assembly 17 will take place in the direction of the double-headed arrow 18 of FIG. 4 resulting in flexing of the leaf spring 22, this leaf spring when no motion is imparted to the grid assembly lying in a plane normal to the plane of the grid assembly and parallel to the longitudinal direction of the strips making up the grid.

OPERATION

The operation of this invention will be evident from the foregoing description. Initially, a patient to be X-rayed is positioned on the table surface 11 and an appropriate film cassette inserted in the tray 14 of the carriage 13. The carriage is then positioned by moving the same longitudinally beneath that portion of the patient of which a radiograph is to be made. When the X-ray unit 12 is energized, the motor 24 described in FIGS. 3 and 4 is simultaneously energized to start the rotor 23 rotating. As each of the successive poles of magnetic responsive material shown in FIG. 3 on the rotor 23 passes the magnet 29, the magnetic coupling will exert a force on the grid assembly 17 having a transverse component. In the view of FIG. 3, the force would tend to move the grid assembly 17 downwardly whereas in the view of FIG. 4 the motion would be to the left. The resilient leaf type spring 22 opposes this motion and when an empty segment between the poles is juxtaposed the magnet 29, the leaf type spring 22 will tend to return the grid assembly to its original position but will actually overshoot this position. The next pole will then again exert a pulling force on the magnet 29 thus repeating the oscillation and putting the grid assembly in an oscillation mode.

There is normally a short period of time from the initial energization of the X-ray machine 12 and its actual generation of X-rays to effect an exposure. This short length of time is required for the cathode filament of the X-ray machine to heat up. During this short time interval, there is sufficient time to initiate movement of the grid assembly to its full oscillation amplitude.

Because of the motion of the grid during exposure, the grid lines will not be reproduced on the finished picture as is well known to those skilled in the art. On the other hand, because of the unique magnetic coupling arrangement to impart motion to the grid assembly its movement is silent in operation and extremely smooth, there being no physical contact whatever between the motivating force and the grid assembly.

The "stiffness" of the resilient leaf type spring 22 the rate of rotation of the rotor 23, and the "gap" between the permanent magnet 29 and a passing pole are all appropriately adjusted to provide the desired frequency of oscillation to optimize the overall desired effect of eliminating the grid lines in the completed picture and yet still properly confining the radiation by the grid strips.

As mentioned heretofore, the "gap" or spacing between the permanent magnet 29 and any one of the poles can be adjusted by loosening the screws 30 and shifting the position of the magnet 29 further from the rotor axis 23.

It will be appreciated from all of the foregoing that the present invention has provided a greatly improved radiographic table wherein problems associated with mechanisms heretofore provided for moving the grid assembly have been overcome.

While the magnetic coupling has been described as a permanent magnet 29 on the grid assembly and magnetic responsive material making up the poles of the rotor, these poles could in turn be permanent magnets and a magnetic responsive block or body provided on the grid holder. Further, equivalent type resilient means could be employed rather than the specific flat leaf type spring disclosed. The invention, accordingly, is not to be thought of as limited to the specific example set forth merely for illustrative purposes.

I claim:

1. A radiographic table with a movable grid assembly in cluding, in combination:

a. a table bed frame;

b. a carriage for a film cassette mounted on said bed frame for longitudinal movement to selected positions between the head and foot of the bed frame;
c. a grid assembly;
d. resilient means mounting said grid assembly to said carriage for transverse oscillating movement;
e. movable magnetic responsive means carried on said carriage; and
f. a magnet in magnetic field coupling relationship to said movable magnetic responsive means secured to said grid assembly, whereby movement of said movable magnetic responsive means past said magnet in a direction having a transverse component results in transverse oscillating movement of said grid assembly relative to said carriage.

2. The subject matter of claim 1, in which said movable magnetic responsive means includes a motor driven rotor positioned adjacent to one side of said grid assembly for rotation substantially in a plane including said grid assembly, said rotor having radially extending poles of magnetic responsive material which successively pass close to said adjacent side of said grid assembly when said rotor rotates, said magnet being secured to said adjacent side.

3. The subject matter of claim 1, in which said resilient means includes means resiliently mounting opposite sides of said grid assembly to said carriage, each means including at least one flat leaf spring lying in a plane generally normal to the plane of said grid assembly and parallel to the longitudinal direction of movement of said carriage, one end of said leaf spring being secured to said carriage and the other end to said grid assembly, the width of the leaf spring measured in the longitudinal direction being sufficient to constrain movement of the grid assembly in a transverse direction, the spring functioning similar to a flexure web.

4. The subject matter of claim 2, including adjustable fastening means for securing said magnet to said adjacent side such that the position of securement of said magnet can be changed to vary its spacing from passing poles of said rotor to thereby vary the degree of magnetic coupling.

* * * * *